United States Patent
Krohn et al.

(10) Patent No.: US 11,931,440 B2
(45) Date of Patent: Mar. 19, 2024

(54) TWO-COMPONENT HAIR CARE AGENT, METHOD FOR THE PRODUCTION OF A COSMETIC AGENT AND USE OF THE TWO-COMPONENT HAIR CARE AGENT

(71) Applicant: Henkel AG & Co. KGaA, Duesseldorf (DE)

(72) Inventors: Rene Krohn, Norderstedt (DE); Erik Schulze Zur Wiesche, Hamburg (DE)

(73) Assignee: HENKEL AG & CO. KGAA, Duesseldorf (DE)

( * ) Notice: Subject to any disclaimer, the term of this patent is extended or adjusted under 35 U.S.C. 154(b) by 846 days.

(21) Appl. No.: 16/715,192

(22) Filed: Dec. 16, 2019

(65) Prior Publication Data
US 2020/0188251 A1 Jun. 18, 2020

(30) Foreign Application Priority Data
Dec. 18, 2018 (DE) .................... 10 2018 222 134.0

(51) Int. Cl.
| A61K 8/31 | (2006.01) |
| A61K 8/34 | (2006.01) |
| A61K 8/36 | (2006.01) |
| A61K 8/37 | (2006.01) |
| A61K 8/41 | (2006.01) |
| A61K 8/46 | (2006.01) |
| A61Q 5/02 | (2006.01) |
| A61Q 5/12 | (2006.01) |

(52) U.S. Cl.
CPC .............. *A61K 8/31* (2013.01); *A61K 8/342* (2013.01); *A61K 8/36* (2013.01); *A61K 8/37* (2013.01); *A61K 8/41* (2013.01); *A61K 8/466* (2013.01); *A61Q 5/02* (2013.01); *A61Q 5/12* (2013.01); *A61K 2800/45* (2013.01); *A61K 2800/88* (2013.01)

(58) Field of Classification Search
CPC ... A61K 8/22; A61K 8/03; A61K 8/04; A61K 8/06; A61K 8/064; A61K 8/0204; A61K 8/18; A61K 8/19; A61K 8/30; A61K 8/31; A61K 8/35; A61K 8/34; A61K 8/342; A61K 8/345; A61K 8/36; A61K 8/365; A61K 8/41; A61K 8/416; A61K 8/92; A61K 8/922
See application file for complete search history.

(56) References Cited

U.S. PATENT DOCUMENTS

| 2003/0075197 A1* | 4/2003 | Kripp ....................... A61Q 5/04 132/205 |
| 2005/0049157 A1* | 3/2005 | MacDonald ........... C11D 3/221 510/130 |
| 2007/0065392 A1* | 3/2007 | Simonnet ................ A61K 8/42 424/70.31 |
| 2008/0025937 A1* | 1/2008 | Cassier .................... A61K 8/46 424/70.2 |
| 2010/0186177 A1* | 7/2010 | Hercouet ................. A61K 8/31 8/408 |
| 2017/0112743 A1 | 4/2017 | Schoepgens et al. |

FOREIGN PATENT DOCUMENTS

| BR | PI0505888 A * | 9/2007 | .......... A61K 31/125 |
| EP | 0471105 A1 | 2/1992 | |
| EP | 1854448 A2 | 11/2007 | |
| WO | WO-03080014 A1 * | 10/2003 | ............... A61K 8/04 |

OTHER PUBLICATIONS

Mintel, Oribe Beatiful Color, Masque, Oribe Hair Care, Mizu Salon, Database Entry No. 1522953, Mar. 2011, http://www.gnpd.com.
Mintel, Conditioner for Dry Hair, Valery Joseph, Valery Joseph Long Nourish, Database Entry No. 2554085, Jul. 2014, http://www.gnpd.com.

* cited by examiner

*Primary Examiner* — Micah Paul Young
(74) *Attorney, Agent, or Firm* — Lorenz & Kopf, LLP

(57) ABSTRACT

The present disclosure relates to a two-component hair care agent including, separately from one another, an anhydrous carrier as a first component and, as a second component, an aqueous carrier. The anhydrous carrier includes a branched or unbranched alkane having a chain length of C10 to C30, a branched or unbranched fatty alcohol having a chain length of C8 to C22, an organic acid or an alkalizing agent and a pH sensitive color indicator. The aqueous carrier includes a cationic surfactant comprising an organic radical having a chain length of C12 to C30. In addition, the present disclosure relates to a method for the production of a cosmetic agent in which the first component and the second component are mixed together and the use of the two-component hair care agent for the care of keratinic fibers, in particular human hair.

19 Claims, No Drawings

TWO-COMPONENT HAIR CARE AGENT, METHOD FOR THE PRODUCTION OF A COSMETIC AGENT AND USE OF THE TWO-COMPONENT HAIR CARE AGENT

CROSS-REFERENCE TO RELATED APPLICATION

This application claims priority to German Patent Application No. 10 2018 222 134.0, filed Dec. 18, 2018, which is incorporated herein by reference in its entirety.

TECHNICAL FIELD

The present disclosure relates to the field of production of hair care agents in cosmetics. In particular, the present disclosure relates to a two-component hair care agent comprising two components having different ingredients provided separately from one another.

BACKGROUND

Cosmetic agents which, apart from, for example, some colorants, usually include only one ready-to-use mixed component, have long been known for the cleaning and/or care of the hair and are regularly improved or adapted to the changing needs of consumers. For example, consumers expect modern hair conditioning agents to clean, smooth, comb easily, soften, gloss, and render hair easy to style, moisturize, protect against dandruff and give hair more volume. There is a variety of active ingredients known which can fulfill one or more of the aforementioned requirements in one such cosmetic agent. However, the presence of a large amount of different active ingredients can destabilize a hair cosmetic, which is why there is usually an attempt to fulfill as many of the aforementioned requirements as possible using a small number of well-tolerated active ingredients.

A wide variety of different components can also limit formulation freedom in the development of cosmetic agents because components interact with one another or interfere with the structure. For example, substances can interfere with the desired structure of an emulsion, wherein the desired structure of the emulsion is directly associated with a certain advantageous cosmetic effect. The formulation freedom is further limited by the requirement for good biodegradability, regulatory limitations, etc. In this respect, it is highly desirable to provide additional degrees of freedom for cosmetic formulations.

The fact that cosmetics appeal to their users on an emotional level is also not an insignificant aspect. Cosmetic products whose use is pleasurable, interesting or otherwise associated with positive emotional experiences will, in simple terms, always be preferred to boring products, even when the achievable end result is equivalent to a cosmetic application.

SUMMARY

The present disclosure described herein has been achieved in view of the above-mentioned requirements or desirable properties and the underlying object is firstly to provide a cosmetic agent, in particular a hair care or conditioning agent, which constitutes an emulsion that can be easily produced. In particular, the agent should provide the possibility of offering maximum formulation freedom. On the other hand, it is also the object underlying the present disclosure to provide a cosmetic agent, in particular a hair care or hair conditioning agent, which offers a certain sense of achievement in the preparation and application.

The object is achieved by a first aspect of the present disclosure described here, a two-component hair care agent which comprises, separately from each other, an anhydrous carrier as a first component and an aqueous carrier as a second component, exemplified in that the anhydrous carrier is a branched or unbranched alkane having a chain length of C10 to C30, preferably from C12 to C24, more preferably from C14 to C20, a branched or unbranched fatty alcohol having a chain length of C8 to C22, preferably C10 to C18, more preferably C12 to C16, an organic acid or an alkalizing agent and a pH-sensitive color indicator, and the aqueous vehicle comprises a cationic surfactant comprising an organic radical having a chain length of C12 to C30, preferably C14 to C26, more preferably C16 to C22.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

It should be noted that "anhydrous" in the context of the present disclosure means that from 0 to about 5% by weight of water, preferably from 0 to about 3% by weight, particularly preferably from 0 to about 1% by weight, most preferably from 0 to about 0.5% by weight of water is present, in each case based on the total weight of the designated "anhydrous" component.

Through such an embodiment described above, the degrees of freedom in the formulation of a cosmetic agent considerably increases, for example, by ingredients that cannot normally be used together, because this would impair storage stability, yet can be used in a product in which they are spatially separated until just before use as constituents of different components, or in which different conditions can be created in the various components, for example, with regard to the pH value or other relevant parameters. This freedom to make the pH value of the components different is actually used in the present disclosure. In this way, various ingredients in the component can be stored with the pH value which is more favorable for their stability, and in addition, a mixing of the components can achieve a pH value more favorable for hair care in the resulting mixture. The storage stability of certain ingredients is significantly increased by this approach. Hydrolysis-sensitive substances in a basic component can thus be provided in acid. The use of many substances in storable cosmetic products is made possible in the first place.

Apart from that already mentioned, the first aspect provides a vivid sense of achievement in the preparation of the cosmetic product for use since the color indicator contained is so chosen to achieve, through an occurring color change, the achievement of a provided desirable mixing ratio and to indicate the uniformity of the mixing by the uniformity of the color change. This gives the user a visual confirmation that the product has been optimally mixed and is to be seen as a positive "do-it-yourself" success experience.

In the two-component hair care agent, the pH-sensitive color indicator preferably shows a color change in the pH range of between about 3 and about 6, preferably a pH between about 3.5 and about 5.5, more preferably a pH between about 4 and about 5, and/or the pH-sensitive color indicator is selected from the group including methyl orange, methyl red, resorcinol yellow, quinaldine red, Congo red, bromocresol green and bromothymol blue.

In the two-component hair care agent of the present disclosure, the color indicator, depending on its color change range, is preferably used in one of the first component and the second component, such that a desired mixing ratio of the first component and the second component, while maintaining and uniformly mixing the first component and the second component, sets a pH value in the resulting mixture in the range from about 3 to about 6, preferably from about 3.5 to about 5.5, particularly preferably from about 4 to about 5, indicated by the color change. Maintaining these pH value ranges results in the best care effect on the hair. Such selection of the indicator and use in the respectively suitable phase ensures that the attainment of the desirable pH value in the ready-to-use mixture and also that a good mixing of the same are safe and reproducible.

The second component preferably has a pH value of from about 2 to about 5, preferably from about 2.5 to about 4.5, more preferably from about 3 to about 4 in the two-component hair care agent. The advantage of this is that at this pH value, stable ingredients that are unstable in other pH ranges can be used, wherein yet, due to mixing with the other component, the hair is not exposed to any pH value unfavorable for hair care.

In the case of the two-component hair care agent, the alkalizing agent is preferably an alkanolamine, which is preferably selected from the group including monoethanolamine, diethanolamine, triethanolamine, and aminomethylpropanol.

In the case of the two-component hair care agent, the acid is preferably an alkylsulfonic acid or a carboxylic acid, wherein the acid is preferably selected from the group including octanoic acid, decanoic acid, methylsulfonic acid, and ethylsulfonic acid.

The above-described alkalizing agents and acids have been found to be particularly suitable for the purposes of the present disclosure. When used, technically advantageous effects described for the present disclosure are achieved to a greater extent.

According to a preferred embodiment, the two-component hair care agent contains as component c) an ether which is an alkoxylated fatty alcohol which preferably has the formula $HO(C_3H_6O)_nC_mH_{2m+1}$, in which n is from about 1 to about 6, preferably from about 2 to about 4, and m is from about 5 to about 14, more preferably from about 6 to about 12, most preferably from about 8 to about 10. In particular, the ethers used as contemplated herein are particularly suitable for the solution of the problem underlying the present disclosure.

The anhydrous carrier contains PPG-3-Caprylyl Ether (INCI), a caprylyl ether containing a tripropylene glycol group as an especially preferred ether.

According to a further preferred embodiment, the two-component hair care agent contains, as a component c), an alkyl ester which is a fatty acid ester. More preferably, the fatty acid ester is a glycerol triester having the same or different acyl groups. More preferably, the acyl groups each have 5 to 11, preferably 7 to 9, carbon atoms.

A most preferred glycerol triester is Capric/Caprylic Triglyceride (INCI).

In the context of the present disclosure described here, these constituents produce a stable foam and also have properties otherwise perfectly suitable for hair care, so that their use in the two-component hair care agent of the present disclosure is technically advantageous.

Furthermore, it is preferable that the two-component hair care agent, in the first component, includes the branched or unbranched alkane in an amount of from about 20 to about 90% by weight, preferably from about 30 to about 80% by weight, more preferably from about 40 to about 70% by weight, most preferably from about 45 to about 65% by weight, based on the total weight of the first component, includes the fatty alcohol in an amount of from about 5 to about 40% by weight, preferably from about 10 to about 37% by weight, more preferably from about 15 to about 34% by weight, most preferably from about 20 to about 30% by weight, based on the total weight of the first component, and includes the pH-sensitive color indicator in an amount of from about 0.0001 to about 0.1% by weight, preferably from about 0.0005 to about 0.05% by weight, more preferably from about 0.001 to about 0.01% by weight, based on the total weight of the first component, and optionally includes the nonionic surfactant in an amount of from about 1 to about 20% by weight, preferably from about 2 to about 15% by weight, more preferably from about 3 to about 10% by weight, based on the total weight of the first component, and/or exemplified in that the two-component hair care agent, in the second component, includes water and, based on the total weight of the second component, from about 0.5 to about 20% by weight, preferably from about 1.5 to about 15% by weight, more preferably from about 2.5 to about 10% by weight cationic surfactant.

When the aforementioned concentration ranges are met, the technically advantageous effect described for the present disclosure can be achieved to a greater extent with increasing extent of adherence. Illustrated by way of example for the color indicator, it is an advantage that in these concentration ranges, a clearly visible coloration, a clearly visible color change and a good visibility of the mixing quality are achieved without achieving a disturbingly high concentration of the color indicator.

In the two-component hair care agent, the volume ratio of the first component to the second component is from about 10 to 1 to about 1 to 10, preferably from about 5 to 1 to about 1 to 5, more preferably from about 2 to 1 to about 1 to 2, most preferably about 1:1. This is advantageous since in this way, in preparation for the application, no excessively small amounts, which would be difficult to meter with good accuracy, have to be dosed.

In the two-component hair care agent, the volume ratio of the first component to the second component particularly preferably is from about 10 to 1 to about 1 to 10, preferably from about 5 to 1 to about 1 to 5, more preferably from about 2 to 1 to about 1 to 2, most preferably about 1:1. This is advantageous since in this way, in preparation for the application, no excessively small amounts, which would be difficult to meter with good accuracy, have to be dosed.

In the two-component hair care agent according to the present disclosure, it is preferable that the first component and the second component are liquid at a temperature of about 20° C. and a pressure of about $10^5$ Pa. The components can thus be easily mixed at common residential and temperature and pressure conditions.

Apart from that already mentioned, it is preferred in the two-component hair care agent of the present disclosure that it contains no oxidizing agent, no substantive dye and no oxidation dye precursor for dyeing keratinic fibers, in particular human hair. One advantage of this is the ease of use, without having to take necessary measures to prevent staining of skin, clothing or bathroom utensils with hair coloring agents.

Apart from the first aspect described above, the object underlying the present disclosure is achieved by a second aspect, a method for producing a cosmetic agent in which the first component and the second component are mixed together. Features described for the first aspect may also be found in the second aspect, unless there is a specific obstacle. The technically advantageous effects of the respective features are as described above for the first aspect and that by such a method, previously non-commercially usable hair care formulations are obtained, which conventional hair care products can achieve superior cleaning and/or care performance.

An advantageous development of the method can be achieved when it is ensured that the pH value of the cosmetic agent is from about 3 to about 6.5, preferably from about 4 to about 6, more preferably from about 4.5 to about 5.5. This range is optimal for hair care. Accordingly, care results of hitherto unavailable quality can be achieved since non-storage-stable compositions can be produced shortly before use and then applied in the optimum pH range.

Apart from the aspects described above, the object underlying the present disclosure is achieved by a third aspect, a use of the two-component hair care agent for the care, preferably for the conditioning, of keratinic fibers, in particular human hair. Previously described features can also be found in this aspect as long as there is no specific obstacle. The realization of the subject of the third aspect leads to superior hair care results. In particular, an advantage is that the hair treated with the products as contemplated herein can benefit from a superior care performance and have to a particularly great extent desirable properties such as softness, brilliance and absence of frizz.

A further subject of the present disclosure is a hair treatment method in which an inventive or inventively preferred two-component hair care agent is applied to the wet or dry hair and either left on the hair until the next hair wash or optionally is rinsed off from the hair after a contact time of from about 1 second to about 30 minutes.

The two-component hair care agent of the present disclosure can be designed, for example, as follows, wherein all percentages are understood to mean by weight based on the total weight of each component and "ad 100" means that the weight percentages lacking about 100 percent by weight are supplemented with the corresponding substance.

Anhydrous Phase Example 1

| | |
|---|---|
| Isododecane | ad 100 |
| Cetearyl alcohol | 9.00 |
| Myristyl alcohol | 15.00 |
| Caprylic/Capric Triglyceride (INCI) | 5.00 |
| Dimethicone 5 cst (INCI) | 30.00 |
| Methyl red | 0.005 |
| Monoethanolamine | 0.005 |
| Perfume | 1.40 |

Anhydrous Phase Example 2

| | |
|---|---|
| Isododecane | ad 100 |
| Cetearyl alcohol | 9.00 |
| Myristyl alcohol | 15.00 |
| Caprylic/Capric Triglyceride (INCI) | 5.00 |
| Dimethicone 5 cst (INCI) | 30.00 |
| Bromothymol blue | 0.005 |
| Monoethanolamine | 0.005 |
| Perfume | 1.40 |

Aqueous Phase

| | |
|---|---|
| Water | ad 100 |
| Sodium benzoate | 0.50 |
| Lactic acid | 0.90 |
| Stearamidopropyl Dimethylamine (INCI) | 0.80 |
| Cetrimonium Chloride (INCI) | 1.50 |

The anhydrous phase of Example 1, as the first component, was mixed with the aqueous phase as a second component in the weight ratio of the first component to the second component 10 to 1 to 1 to 10, preferably 5 to 1 to 1 to 5, more preferably 2 to 1 to 1 to 2, most preferably 1:1. This was done by vigorous shaking by hand.

The aqueous phase of Example 2, as the first component, was mixed with the aqueous phase as a second component in the weight ratio of the first component to the second component 10 to 1 to 1 to 10, preferably 5 to 1 to 1 to 5, more preferably 2 to 1 to 1 to 2, most preferably 1:1. This was done by vigorous shaking by hand.

The two hair care agents thus obtained were applied to dry or damp hair and rinsed with lukewarm water after a contact time of 5 minutes at 20° C. The thus treated hair was soft and had a nice shine.

The then re-dried hair was smooth and not curled (absence of frizz).

In a modification of the hair treatment method as contemplated herein, the hair care agents obtained were sprayed onto the dry hair using a pump sprayer. The hair thus treated was soft, had a nice shine and was not curled (absence of frizz).

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

What is claimed is:

1. A two-component hair care agent comprising, separately from each other, an anhydrous carrier as a first component and an aqueous carrier as a second component, wherein the anhydrous carrier comprises
a) a branched or unbranched alkane having a chain length of C10 to C30,
b) a branched or unbranched fatty alcohol having a chain length of C8 to C22,
c) an organic acid or an alkalizing agent, and
d) a pH-sensitive color indicator, and the aqueous carrier comprises a cationic surfactant comprising an organic radical having a chain length of C12 to C30;

wherein the anhydrous carrier and the aqueous carrier are free from an oxidizing agent, a substantive dye, or an oxidation dye precursor for dyeing keratinic fibers.

2. The two-component hair care agent according to claim 1, wherein the pH-sensitive color indicator is selected from the group of methyl orange, methyl red, resorcinol yellow, quinaldine red, bromocresol green, and bromothymol blue.

3. The two-component hair care agent according to claim 1, wherein the second component has a pH of from about 2 to about 5.

4. The two-component hair care agent according to claim 1, wherein the alkalizing agent is an alkanolamine selected from the group of monoethanolamine, diethanolamine, triethanolamine and aminomethylpropanol.

5. The two-component hair care agent according to claim 1, wherein the organic acid is an alkylsulfonic acid or a carboxylic acid.

6. The two-component hair care agent according to claim 1, wherein the cationic surfactant is a trimethylalkylammonium halide, an N-[3-(dimethylamino) propyl]alkanamide, or an esterquat.

7. The two-component hair care agent according to claim 1, wherein the two-component hair care agent further comprises as a constituent e) an alkyl ester or an ether in the aqueous carrier, wherein a total carbon atom number of the alkyl ester or the ether is from 6 to 30.

8. The two-component hair care agent according to claim 7, wherein the constituent e) is the ether, and wherein the ether is an alkoxylated fatty alcohol.

9. The two-component hair care agent according to claim 8, wherein the alkoxylated fatty alcohol has the formula $HO(C_3H_6O)_nC_mH_{2m+1}$, wherein n is from about 1 to about 6, and m is from about 5 to about 14.

10. The two-component hair care agent according to claim 8, wherein the alkoxylated fatty alcohol is PPG-3 Caprylyl Ether (INCI).

11. The two-component hair care agent according to claim 1, wherein the alkane is liquid in undissolved form at a temperature of about 20° C. and a pressure of about $10^5$ Pa.

12. The two-component hair care agent according to claim 1, wherein the alkane is a branched C20 to C30 alkane or is a linear C8 to C14 alkane.

13. The two-component hair care agent according to claim 1, wherein:
the first component includes the branched or unbranched alkane in an amount of from about 20 to about 90% by weight based on the total weight of the first component, the fatty alcohol in an amount of from about 5 to about 40% by weight based on the total weight of the first component, the pH-sensitive color indicator in an amount of from about 0.0001 to about 0.1% by weight, based on the total weight of the first component, and optionally includes a nonionic surfactant in an amount of from about 1 to about 20% by weight based on the total weight of the first component; and/or
the second component includes water and, based on the total weight of the second component, from about 0.5 to about 20% by weight of the cationic surfactant.

14. The two-component hair care agent according to claim 1, wherein a weight ratio of the first component to the second component is from about 10 to 1 to about 1 to 10.

15. The two-component hair care product according to claim 1, wherein the first component and the second component are liquid at a temperature of about 20° C. and a pressure of about $10^5$ Pa.

16. A method for the production of a cosmetic agent comprising the step of mixing an anhydrous carrier as a first component and an aqueous carrier as a second component, wherein the anhydrous carrier comprises
a) a branched or unbranched alkane having a chain length of C10 to C30,
b) a branched or unbranched fatty alcohol having a chain length of C8 to C22,
c) an organic acid or an alkalizing agent, and
d) a pH-sensitive color indicator,
and the aqueous carrier comprises a cationic surfactant comprising an organic radical having a chain length of C12 to C30;
wherein the anhydrous carrier and the aqueous carrier are free from an oxidizing agent, a substantive dye, or an oxidation dye precursor for dyeing keratinic fibers.

17. The method according to claim 16, wherein the pH value of the cosmetic agent is from about 3 to about 6.5.

18. A two-component hair care agent comprising, separately from each other, an anhydrous carrier as a first component and an aqueous carrier as a second component, wherein the anhydrous carrier comprises
a branched or unbranched alkane having a chain length of from 14 to 20 carbon atoms,
a branched or unbranched fatty alcohol having the formula $HO(C_3H_6O)_nC_mH_{2m+1}$, wherein n is from about 1 to about 6 and m is from about 5 to about 14,
a glycerol triester having from 5 to 11 carbon atoms,
an alkanolamine, and
a pH-sensitive color indicator showing a color change in a pH range of from about 4 to about 5, and
wherein the aqueous carrier comprises N-[3-(dimethylamino) propyl]octadecanamide and water;
wherein the anhydrous carrier and the aqueous carrier are free from an oxidizing agent, a substantive dye, or an oxidation dye precursor for dyeing keratinic fibers.

19. The two-component hair care agent according to claim 18 wherein:
the alkane is present in an amount of from about 45 to about 65% by weight, based on the total weight of the first component;
the fatty alcohol is present in an amount of from about 20 to about 30% by weight, based on a total weight of the first component;
the glycerol triester is present in an amount of about 5% by weight, based on a total weight of the first component;
the alkanolamine is present in an amount of about 0.005% by weight, based on a total weight of the first component; and
the pH-sensitive color indicator is present in an amount of from about 0.001 to about 0.01% by weight, based on a total weight of the first component.

* * * * *